United States Patent [19]

Sadlier et al.

[11] 4,105,028
[45] Aug. 8, 1978

[54] POSITIVE CONTROL INTRAVENOUS FLUID ADMINISTRATION

[76] Inventors: Patricia M. Sadlier, 620 Second St., Brooklyn, N.Y. 11215; Edward Willett, 44 West End Ave., New York, N.Y. 10024

[21] Appl. No.: 731,771

[22] Filed: Oct. 12, 1976

[51] Int. Cl.² ............................................ A61M 5/16
[52] U.S. Cl. ........................ 128/214 E; 128/DIG. 13; 73/194 E; 137/487.5; 222/59; 222/76; 340/608; 340/609
[58] Field of Search ........... 128/214 E, 214 F, 214 Z, 128/DIG. 12, DIG. 13; 222/59, 52, 76; 137/486, 487.5; 340/239 R; 251/4; 73/194 E

[56] References Cited

U.S. PATENT DOCUMENTS

| | | | |
|---|---|---|---|
| 3,252,623 | 5/1966 | Corbin et al. | 222/59 |
| 3,390,577 | 7/1968 | Phelps et al. | 73/194 E |
| 3,624,800 | 11/1971 | Swick | 251/4 |
| 3,631,437 | 12/1971 | Campbell et al. | 340/239 R |
| 3,790,042 | 2/1974 | McCormick et al. | 222/52 |
| 3,800,794 | 4/1974 | Georgi | 128/214 E |
| 3,890,968 | 6/1975 | Pierce et al. | 128/214 E |
| 4,037,598 | 7/1977 | Georgi | 128/214 E |
| 4,038,981 | 8/1977 | LeFeure et al. | 128/214 E |
| 4,038,982 | 8/1977 | Burke et al. | 128/214 E |

*Primary Examiner*—Dalton L. Truluck
*Attorney, Agent, or Firm*—Hane, Roberts, Spiecens & Cohen

[57] ABSTRACT

A method and apparatus for parenteral administration of medical fluids has a normally closed clamp on the intraveneous feeding tube which is opened by means of an electromagnetic actuator at a preselected drop frequency rate and closed when a drop is detected by a conductive path established by the drop passing between two opposing electrodes. The electrical system governing the drop counting electrodes also is provided with drop size measuring means which acts to control the preselected drop frequency rate wherein a desired volumetric rate is maintained. Safety features are also provided to prevent excessive or insufficient flow rates.

15 Claims, 14 Drawing Figures

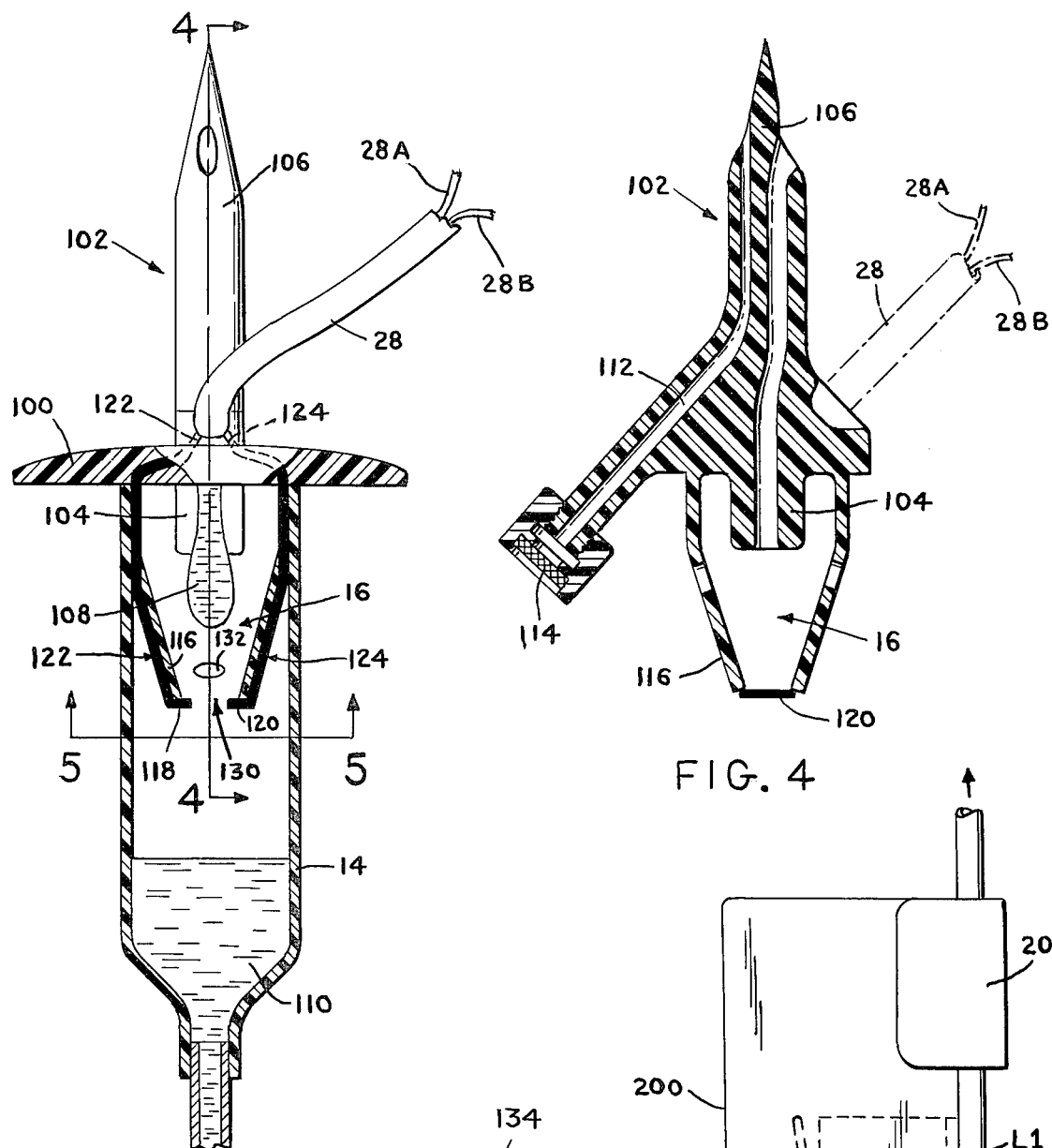
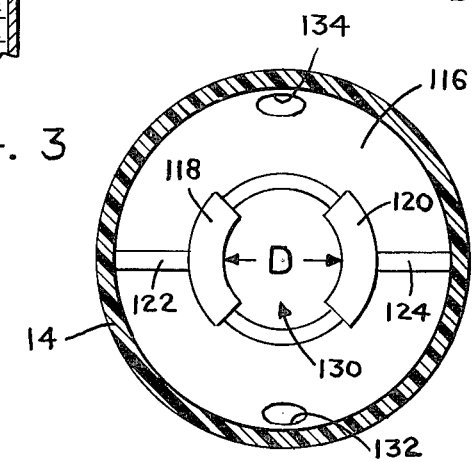
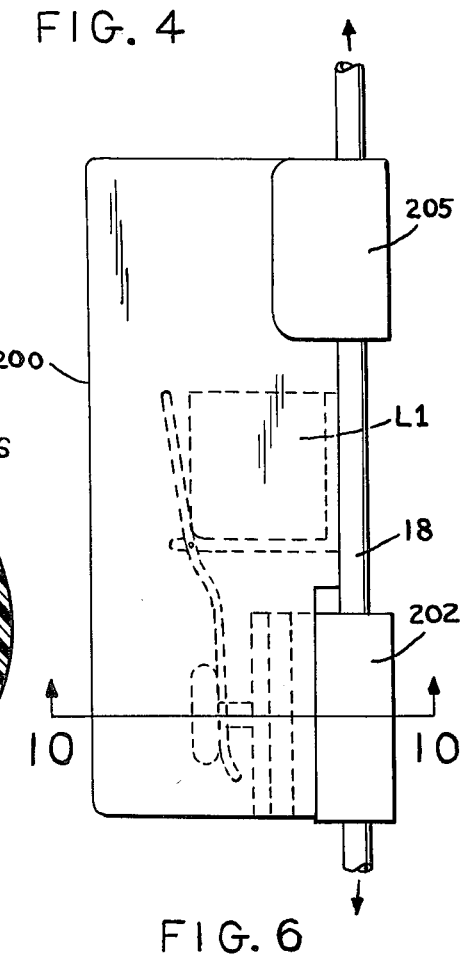
FIG. 3
FIG. 4
FIG. 5
FIG. 6

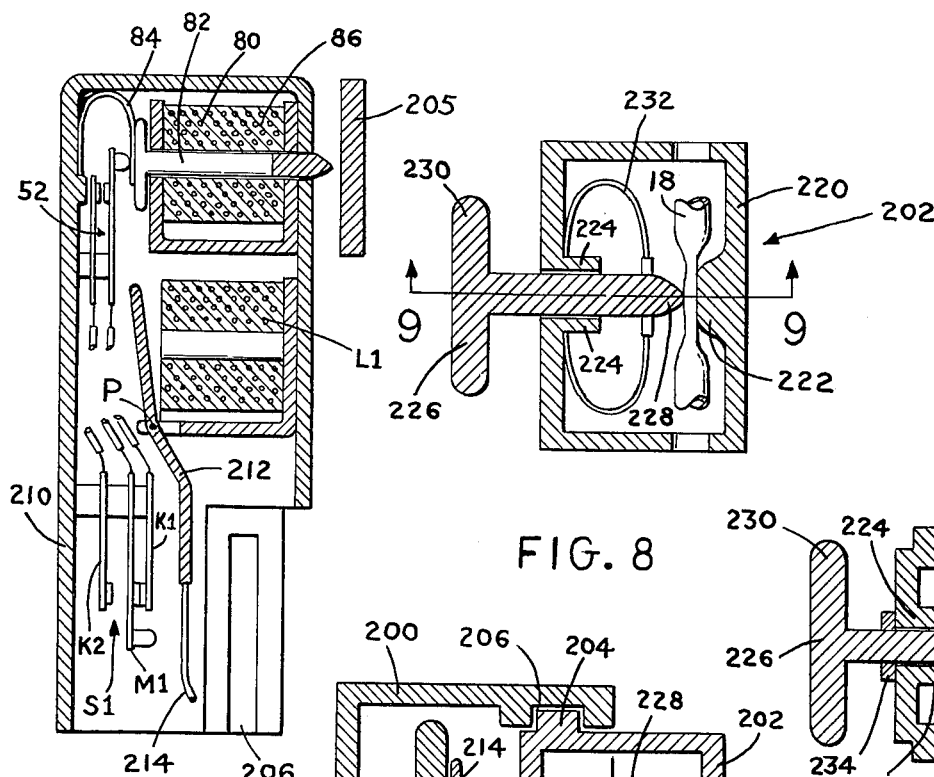
FIG. 7
FIG. 8
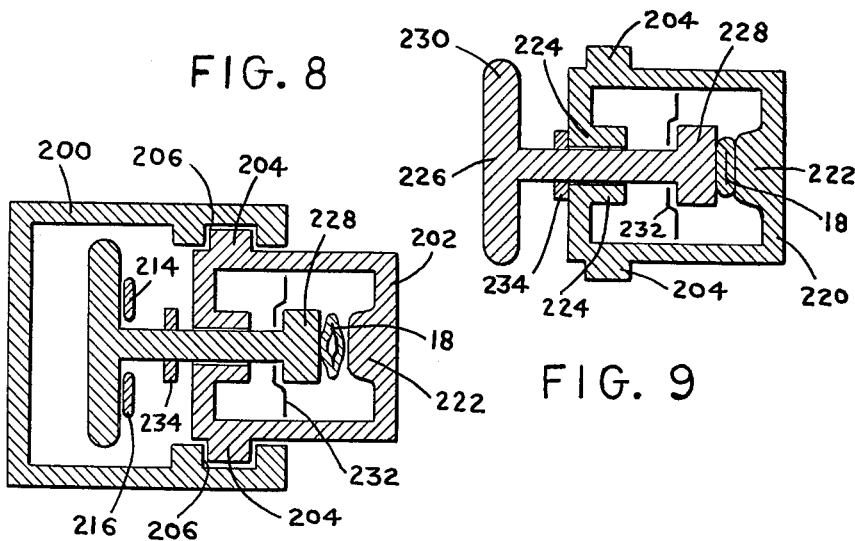
FIG. 9
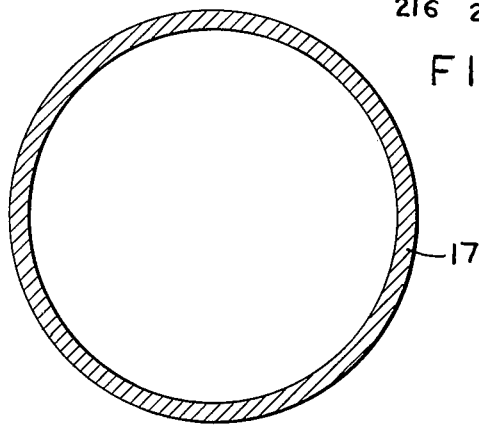
FIG. 10
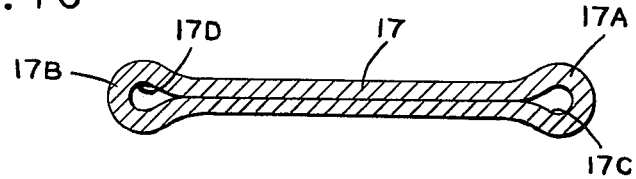
FIG. 11
FIG. 12
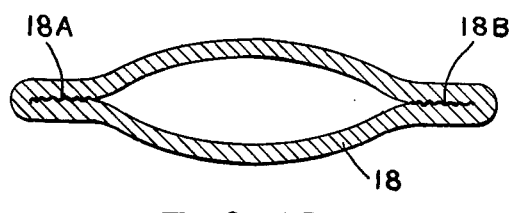
FIG. 13
FIG. 14

POSITIVE CONTROL INTRAVENOUS FLUID ADMINISTRATION

BACKGROUND OF THE INVENTION

This invention relates to an improved method and apparatus for the precise administration of parenteral fluids whereby a clamp is repeatedly opened and closed to yield an exact, predetermined volumetric flow rate under an extremely wide range of operating conditions.

The common method of intravenous fluid administration involves connecting an inverted flask of nutrient fluid to a closed tubing system which transports the fluid to a needle or cannula within the venous system of a patient. The flow of liquid is maintained by the force of gravity operating on the elevated liquid column. The flow rate is controlled by a manually operated clamp which changes the internal cross-sectional area of the tubing. Flow rates are measured by means of a drip chamber located at the upper end of the tubing system. The fluid from the flask passes through a drop former in the drip chamber. The drip chamber serves the dual function of allowing a nurse or other attendant to observe the rate at which the liquid drips out of the bottle, and also creates a reservoir for the liquid at the lower end of the chamber to ensure that no air enters the main feeding tube leading to the patient. For most administrations the drop formers used produce approximately 15 drops per milliliter. When slower administration of fluid is desired, drop formers producing approximately 60 drops per milliliter are used. It is general practice in most hospitals for the nurse to periodically monitor flow rates by counting the number of drops within a specific time interval. The nurse will mentally perform the mathematics necessary to convert the timed drop count to an appropriate rate, e.g. in cubic centimeters per hour.

Precise regulation of the flow rate requires time consuming clamping adjustments when the intravenous system is set up by the nurse. Relatively constant surveillance is required to maintain a stable flow rate due to physiological fluctuations, changes in the mechanical conditions of the intravenous system, or to exhaustion of liquid supply when the flask is empty. In most hospital situations, continuous monitoring of intravenous systems is neither practical nor economically feasible. Periodic monitoring is prone to error and may seriously compromise patient safety and the effectiveness of medical therapy. Accurately controlled flow rates are needed in a number of situations, such as with eldery, cardiac, obstetrics and pediatric patients in which precise fluid volumes or pharmacological doses are to be infused. This is increasingly important because intravenous therapy is becoming a more routine procedure.

In recent years a number of electronic monitoring systems, drop flow controllers and infusion pumps have been developed to accomplish the various tasks of sensing and regulating drop flow rates. The automatic flow controllers as proposed in the past basically compare a reference drop rate to the actual drop rate. This comparison yields an error signal used to control some kind of flow adjustment apparatus. Various methods of detecting drop frequency have been proposed utilizing optical, thermal, mechanical, conductive, electromagnetic or capacitive means. Some of the fluid control means have included electromagnetically operated pressure clamps and check valves. All of these systems have not always proved to be entirely satisfactory because they are feedback control systems in which the transfer function of the system is not well known, or indeed, constant in time. Consequently the response time of such systems cannot be very rapid, and over short periods of time flow rates can be significantly different from those desired. In most of these systems no account is taken of the variation of drop size. Variations in the patient condition such as fluctuations in intravascular pressure are not readily determined by the current monitoring methods.

Typical monitoring systems are shown in U.S. Pat. Nos. 3,890,968; 3,756,556; 3,736,930; 3,790,042; 3,826,137; 3,469,574 and 3,800,794.

SUMMARY OF THE INVENTION

Generally briefly stated the invention contemplates a method and apparatus for parenteral administration of medical fluids wherein a normally closed clamping means on an intravenous feeding tube is opened at a preselected drop frequency rate and closed when a drop is detected by a conductive path established when the drop passes a sensor means.

More specifically, the invention utilizes a positive control concept of the drop flow administration for the parenteral delivery of medical liquids. The rate of drop formation is precisely controlled by periodically opening a normally closed clamping means to free flow conditions on the intravenous tubing at an exact preselected rate. A drop detector based upon electrical conductivity of the parenteral liquid detects the formation of a drop and closes the clamp. In this manner drop rate is exactly equal to the preselected drop frequency.

The concept of a binary control of the clamping means wherein a free running pulse source generates a first signal to open the clamping means and a drop detector generates a second signal to close the clamping means has many advantages over the heretofore used analog systems wherein error voltages were generated to control the degree of opening of the clamping means. For example, drop frequency is essentially independent of the patient's condition. Exact flow rates within a wide dynamic range, typically a 100 to 1 range can be achieved. The size of the drop can be derived from the second signal, and this information can be used to vary the drop rates to establish an exact volumetric flow rate for the medication. The time between the first signal and the second is a measure of the patient's condition and the apparatus function.

In addition, since a normally closed clamping means is wide open during the entire drop generation period, there is insignificant pressure loss in the tubing subsystem during the drop generation period which is also the period when fluid is delivered to the patient. Thus all of the pressure developed by the column of liquid is available to force flow through minor obstructions and the instantaneous high flow rate also serves to prevent clotting especially when low drop rates are used.

Although drop rates are usually specified in IV (intravenous) therapy, volumetric flow rates are usually implied. However, the size of the drops formed may vary with time, flow rate, type of liquid being delivered, etc. Hence, fixed drop rates could mean variable volumetric flow rates. Thus, knowing the size of the drops allows the drop rate to be modified such as to yield a constant volumetric flow rate.

It is therefore a feature of the invention to provide a drop detector which will give indications of drop size.

BRIEF DESCRIPTION OF THE DRAWINGS

Other objects, features and advantages of the invention will be apparent from the following detailed description when read with the accompanying drawing which shows the presently preferred embodiment of the invention.

In the drawings:

FIG. 3 is a cross-sectional view of the drop detector and drop chamber of FIG. 1;

FIG. 4 is a cross-section taken along the line 4—4 of FIG. 3;

FIG. 5 is a cross-sectional view taken along the line 5—5 of FIG. 3;

FIG. 6 is a side view partially in phantom of an electromechanical clamping means;

FIG. 7 is a vertical cross section of the actuator portion of the clamping means of FIG. 6;

FIG. 8 is a vertical cross-section of the clamping portion of the clamping means of FIG. 6;

FIG. 9 is a sectional view taken along line 9—9 of FIG. 8;

FIG. 10 is a sectional view taken along line 10—10 of FIG. 6;

FIG. 11 shows the cross section of a conventional unclamped IV tubing;

FIG. 12 shows the tubing of FIG. 11 when clamped;

FIG. 13 shows the cross section of a piece of unclamped IV tubing in accordance with a feature of the present invention; and FIG. 14 shows the tubing of FIG. 13 when clamped.

DESCRIPTION OF THE PREFERRED EMBODIMENT

Figure 1:
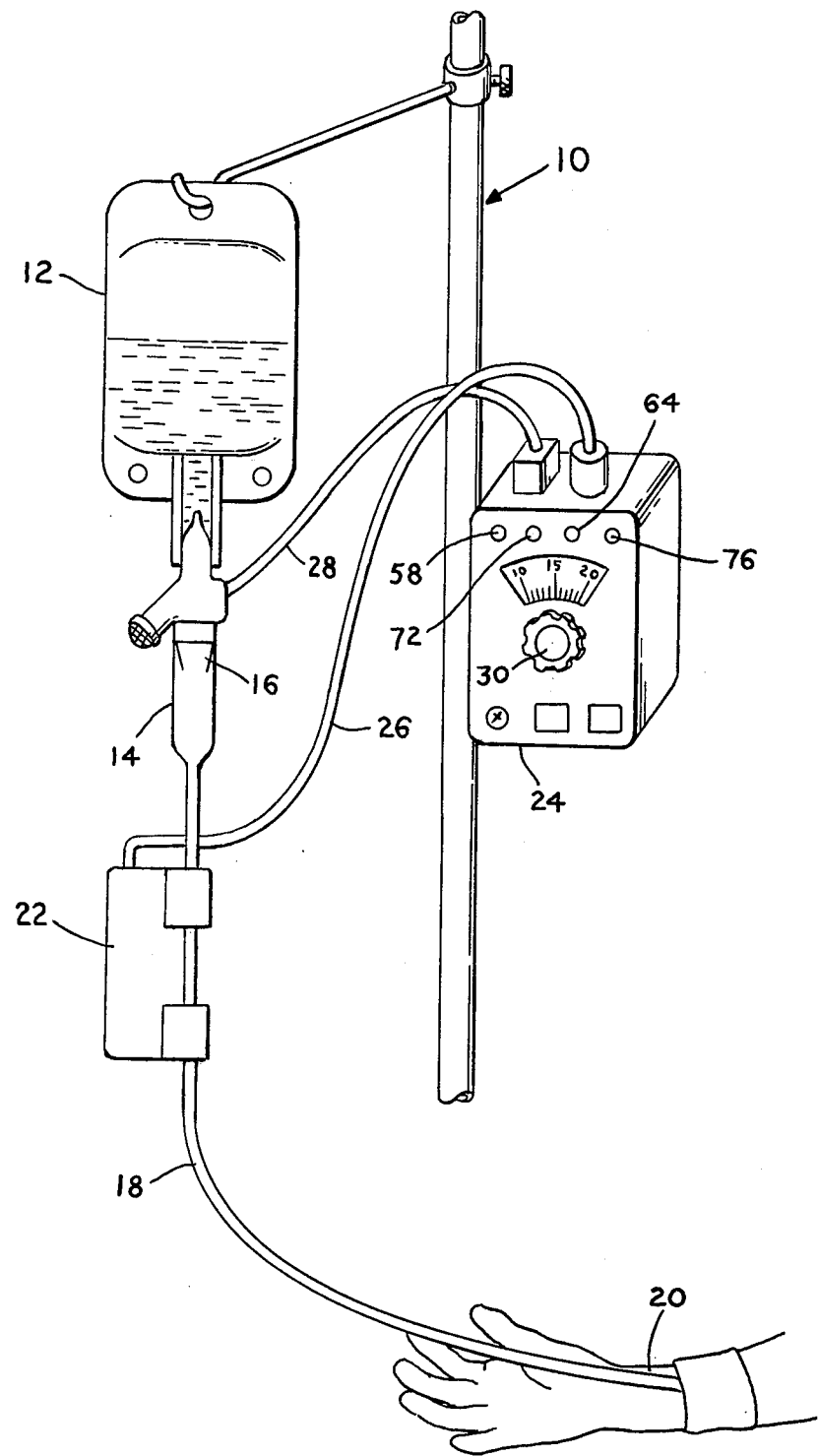
FIG. 1 shows a perspective view of a positive control intravenous fluid administration system constructed in accordance with the present invention.

In FIG. 1 there is shown a positive control intravenous fluid administration system wherein a stand 10 supports an IV flask 12 containing IV fluid for delivery via a drop chamber 14, a drop detector 16 and a tube or tubing 18 to a patient 20. The flow of fluid is controlled by means of an electromechanically actuated clamp 22 in response to signals from control unit 24 via leads in cable 26. In addition, each time drop detector 16 senses a drop it transmits a signal via leads in a cable 28 to control unit 24.

Generally, the system operates as follows. The desired drop rate is set by adjusting knob 30 of control unit 24. Thereafter, clamp 22 periodically receives an actuation signal on the leads of cable 26 and is periodically opened at this desired drop rate. As in a conventional intravenous fluid administration system, no drop is formed until the clamp is opened. Once, the clamp 22 is opened it remains open until a drop is formed in drip chamber 14 and passes through drop detector 16. At that time a signal is fed back via the leads of cable 28 to control unit 24 which then terminates the actuation signal. The clamp 22 closes and remains closed until the next actuation signal occurs.

Figure 2:
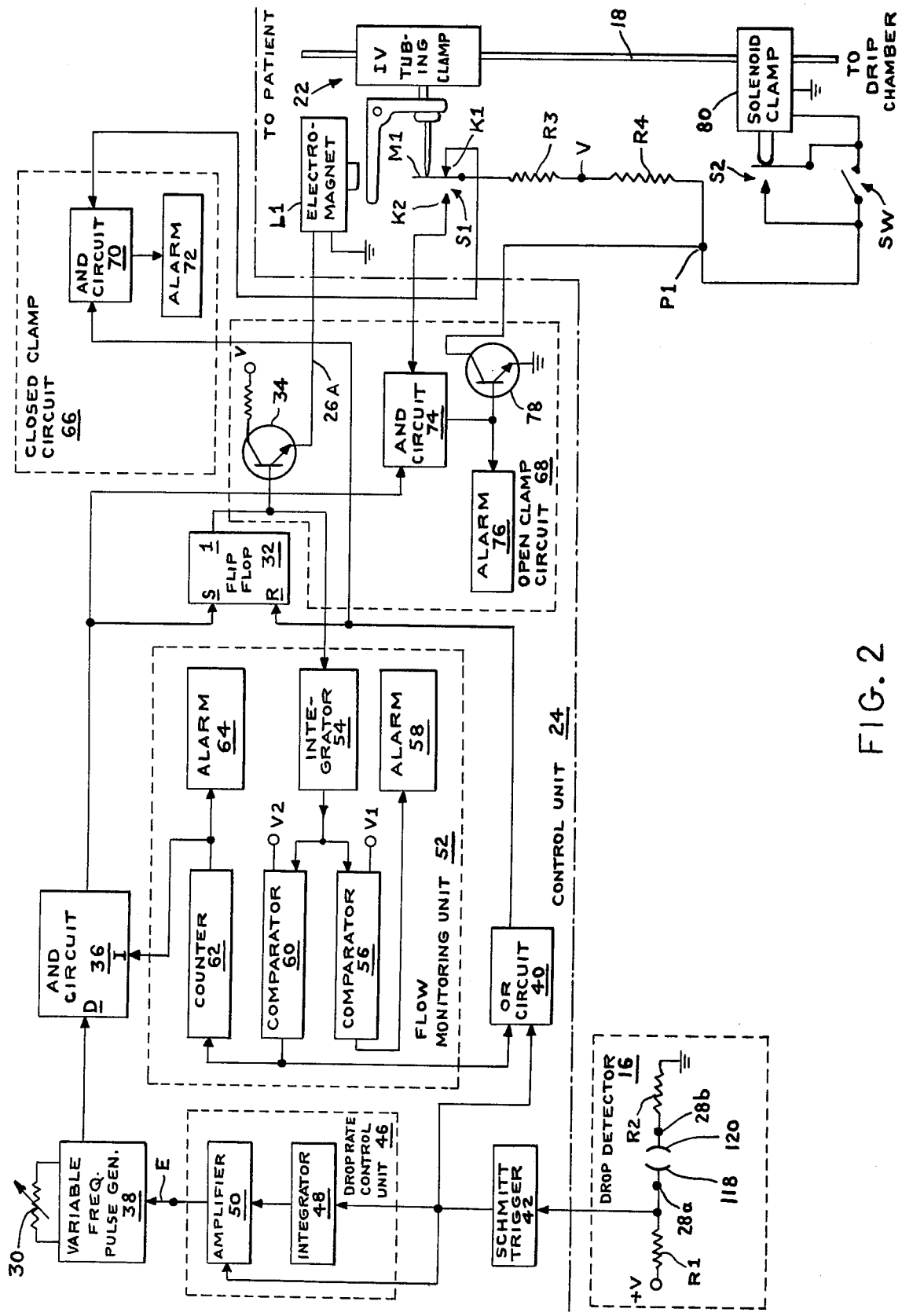
FIG. 2 is a block diagram of the system of FIG. 1.

The details of the system will be described with respect to the block diagram of FIG. 2. Generally, the control unit 24 centers around set-reset flip-flop 32 whose 1-output is connected via switching transistor 34 acting as a current driver and leads 26A to the electromagnet 1 of clamp 22. The S-input of flip-flop 32 is connected to the output of AND-circuit 36 which has an input connected to the output of variable frequency pulse generator 38. The R-input of the flip-flop 32 is connected to the output of OR-circuit 40 which has an input connected to the output of Schmitt trigger circuit 42 whose input is connected to the output of drop detector 16.

The operation of this fundamental system will now be described assuming: AND-circuit 36 is enabled; the voltage on line E, the operating voltage for the pulse generator has a fixed value; and the flip-flop 32 has been reset. The desired drop rate is set by adjusting a variable resistor connected to knob 30 which is part of the timing circuit of the pulse generator 38. Accordingly, pulse generator 38 may be set, for example, to 120 pulses per second. Pulse generator 38 acting as a source of control signals will periodically emit a pulse via AND-circuit 36 to the S-input of flip-flop 32. Flip-flop 32 acting as a bistable means in response to this pulse will be set to a first stable state wherein the 1-output thereof goes to a high state turning on switching transistor 34 which emits a signal on line 26A to actuate clamp 22 to its open condition. The clamp will remain open as long as the flip-flop 32 is in this first stable state. Sometime thereafter a drop is formed and detected by drop detector 16 which emits a signal to Schmitt trigger 42 which shapes and amplifies this signal into a constant amplitude pulse. The pulse is fed via OR-circuit 40 as a second control signal to the R-input of flip-flop 32. Upon receipt of the pulse at the R-input, flip flop 32 switches to its other stable state wherein the signal on the 1-output goes low, turning off switching transistor 34 and deactivating clamp 22. The clamp closes and blocks the intravenous tubing, preventing the formation of another drop until another pulse is emitted by pulse generator 38. Thus, it is seen that the drop rate is controlled by the frequency of the pulses from pulse generator 38.

If one desired to control volumetric flow rate instead of drop rate it is necessary to use a drop detector 16 as hereinafter more fully described in conjunction with the drop rate control unit 46 which controls the amplitude of operating voltage E of the pulse generator 38. Assume for the present that the greater the amplitude of voltage E, the lower the pulse repetition frequency. As will hereinafter become apparent the electrodes 118 and 120 of the drop detector 16 are at the truncated apex of a cone on outputs of a funnel of insulative material. The opposed electrodes define a quasi-circular aperture whose diameter is somewhat less than the smallest drop that can be formed. Thus, as a drop passes through the electrodes it is elongated to an extent that depends upon its size. Accordingly, the time of contact closure is a strong function of drop size and this time can be used to adjust the time when the next drop is initiated, i.e., the time the next pulse is emitted by pulse generator 38. In particular, the drop detector 16 emits a pulse (drop detection signal) whose width is a function of drop transit time. This pulse shaped by Schmitt-trigger 42 is fed to integrator 48. Since the pulse is of constant amplitude integrator 48 emits a ramp voltage whose amplitude linearly increases with time. The ramp voltage is fed, via sample and hold amplifier 50 which is triggered by the trailing edge of the pulse from Schmitt-trigger 42, as a control voltage to pulse generator 38.

It should be noted that this feature of the invention is highly suited in situations where highly viscous fluids are delivered via filters or when high arterial pressures are encountered presenting a need for forces greater than the hydrostatic gravity produced force. To maintain the desired flow rate it is possible to use air pressure in the intravenous flask. Under these conditions the flow rate may be so high that it will produce continuous fluid flow instead of a drop formation. The system will continue to work. As soon as the liquid bridges the gap between the drop detector electrodes a signal is generated to close the clamp. Because of continuous flow conditions the amount of liquid produced will be much larger than the ordinary drop. However, this increase in drop size will be reflected as an increase in duration of the drop detection signal, and this information is used to adjust the time for the next drop initiation pulse by pulse generator 38 so that volumetric flow rate is maintained at the exact rate desired.

Drop generation time, the time between the pulse from pulse generator 38 initiating drop generation and the drop detector pulse from drop detector 16 is primarily dependent on the condition of the patient. Wide open flow rates can exceed 120 drops per minute (for a 15 drops per milliliter drop former). If the patient's condition changes due to tissue infiltration, incipient clotting, higher venous pressure or tubing kinks, the wide open drop rate could drop to 60 drops per minute. These changes in patient condition require immediate attention by medical personnel if proper IV therapy is to be maintained. An increase in drop generation time signals these changes in patient condition and such an increase is easily determined by another feature of the present invention.

In particular, the 1-output of flip-flop 32 which is high during the entire drop generation time is fed to integrator 54 which is similar to integrator 48. The output of integrator 54 is fed to one input of comparator 56 whose other input is connected to a reference voltage V1. If the amplitude of the ramp voltage from integrator 54 exceeds the amplitude of reference voltage V1 then comparator 56 emits a signal to partial blockage alarm 58. The amplitude of the voltage V1 is chosen to represent a particular drop generation time such as 60 drops per minute.

The flow monitoring unit 52 will also give an alarm when there is no fluid flow at all such as when an IV flask becomes empty. In this case, the output of integrator 54 is fed to a comparator 60 whose reference voltage V2 is set to an amplitude representing, say one drop a minute. Thus, after flip-flop 32 has been set for 1 minute comparator 60 emits a signal which passes through OR-circuit 40 to reset the flip-flop 32. At the same time the leading edge of the signal sets pulse counter 62 to a count of one. The next occurring set pulse from pulse generator 38 again sets flip-flop 32. If the flip-flop remains set for another minute comparator 60 emits another signal which again restores flip-flop 32 and increases the count to two in counter 62. After a predetermined number of such cycles, say six, the counter 62 emits a signal which is fed to no flow alarm 64 and to the inhibiting input I of AND-circuit 36. Thus, the pulses from generator 38 no longer reach the S-input of flip-flop 32 and the clamp is locked in the closed state.

The closed clamp alarm circuit 66 is provided to give an indication when the system is stuck in the closed clamp state. In particular, the clamp 22 should be open when a stop pulse is passed by OR-circuit 40 to restore the flip-flop 32 so that the tubing can be closed. Thus, if the clamp is closed at this time it is known that the clamp is stuck in the closed state. Accordingly, the double pole single throw switch S1 has its normally open contest K1 connected to an input of AND-circuit 70 whose other input is connected to the output of OR-circuit 40. The movable contact M1 of the switch is mechanically connected to the plunger of clamp 22 and electrically connected via a resistor R3 to a source of voltage V. Thus, when the plunger of the clamp 22 is in the retracted state, i.e., the clamp is closed, then AND-circuit 70 is enabled. If at that time a stop pulse is emitted by OR-circuit 40 the closed clamp alarm 72 is actuated.

Similarly, the open clamp circuit 68 is provided to give an indication when the system is stuck in the open clamp state. In particular, the clamp 22 should be closed whenever a start pulse is fed from AND-circuit 36 to set the flip-flop 32 and open the clamp 22. Thus, if the clamp is open at that time it is stuck in the open state. Accordingly, the normally closed contact K2 of switch S1 is connected to one input of AND-circuit 74 whose other input is connected to the output of AND-circuit 36. Thus, if the plunger of clamp 22 is in the extended position the pulse from AND-circuit 36 will trigger alarm 76.

Since the stuck-to-open condition of clamp 22 can result in over infusion it is highly desirable to take further precautions. Therefore, an auxiliary electromechanical clamp 80 controls flow through the tubing 18. The normal condition of the clamp is closed, i.e., in the absence of energization the clamp blocks the flow of fluid in the tubing 18. At the start of operation when the user turns on power the switch SW is momentarily closed and current flows from source V, via resistor R4, switch SW and the coil of the clamp to ground. The clamp 80 is energized, opening the tubing and closing the holding contact set 52 in shunt with switch SW. The clamp will now be held open regardless of the position of switch SW. The pulse that triggers alarm 78 turns on a switching transistor 78 which grounds point P1 causing the deenergization of the clamp 80. Thus, the tubing is closed shut and no fluid can reach the patients.

The various elements of the system of FIG. 2 will now be described in detail.

Flip-flop 32 is a conventional set-reset flip-flop which delivers a high voltage from its 1-output when set and a low voltage when cleared or restored. The switching transistor 34 is a power transistor that switches between conducting and non-conducting states in response to signals received at its base electrode. The AND-circuit 36 can be a conventional two-input AND-circuit wherein the I input inverts the signal. Therefore, the output of the circuit is high only when the D input is high and the I input low. The varaible frequency pulse generator 38 can be a conventional relaxation oscillator utilizing a thyristor having an RC timing network wherein the resistance of the resistor is controllably variable and the firing voltage is controlled by voltage E. The OR-circuit 40 is a conventional two-input OR-circuit whose output is high only when one or more of its inputs are high. Schnitt trigger 42 is a conventional bistable device which is turned on when the input signal drops to a certain negative level and remains on until the input signal rises above that level. Integrators 48 and 54 are conventional operational amplifiers having capacitance feedback to perform the integration. Amplifier 50 is a conventional sample-and-hold circuit which when triggered on samples the amplitude of the signal at its input and stores that amplitude signal in a capacitor in its output circuit. Comparators 56 and 60 can be conventional operational amplifiers operating as difference amplifiers that indicate which of the signals at its two inputs is the greater. The counter 22 can be for example an n-stage shift register or even a cascaded binary counter which emits a pulse from its output after n-pulses have been fed to its input. The alarms can take many forms such as lights, bells, etc. The AND-circuits 40 and 74 are conventional two-input circuits which yield a high output only when both inputs are high. Transistor 78 is a conventional current switching transistor.

The drop detector 16 is shown comprising the resistor R1, the electrodes 118 and 120 and the resistor R2 connected in series between ground and a positive voltage +V. When no drop is bridging the electrodes the signal on line 28A is high when a drop is present, the signal is low. Although many drop detectors can be used for the basic system and particularly the one shown in FIG. 2 of the U.S. Pat. No. 3,790,042, there is preferred, especially when volumetric control is desired, the drop detector shown in FIGS. 3, 4 and 5.

In FIGS. 3, 4 and 5 the drop detector 16 is shown fixed to the collar 100 of piercer 102 and surrounding drop former 104. Slipped over detector 16 and frictionally fitted thereto is drip chamber 14. Connected to the bottom of the drip chamber is tubing 18. The piercer 102 includes a pointed conduit 106 for insertion in an IV flask whereby fluid can pass to the drop former 104 to produce a drop 108 which falls through the drop detector 16 to the drip chamber 14 where it is reservoired as liquid 110. In order to prevent the buildup of vacuum in the flask the second conduit 112 connects the flask via an air filter 114 to atmospheric pressure.

The drop detector 16 comprises a funnel member 116 preferably in the form of a truncated cone of insulating material such as a plastic. The narrower or output end of the funnel member is bordered by a pair of spaced arcuate electrodes 118 and 120. The spacing D between the electrodes is chosen such that the smallest drop passing between the electrodes must contact both the electrodes. Electrical conductors 122 and 124 extend from the electrodes along the outer wall of the funnel member through the piercer to leads 28A and 28B, respectively, of cable 28. Thus, whenever a drop passes through opening 130 leads 28A and 28B are connected in series.

It should be noted that each of the electrodes preferably defines 90° of a circle and are separated from each other along the circumference of such circle by 90°. This configuration minimizes erratic detection pulses if the gap were larger. In addition, to prevent the building of vacuum in the funnel chamber air vents 132 and 134 are cut in the funnel member 116.

In FIG. 6 there is shown the electromagnetically operated clamp 22 comprising an actuator 200 and a clamp assembly 202. The assembly 202 is mounted in the actuator by means of ridges 204 of the assembly sliding into tracks 206 of the actuator (see FIG. 10). In addition a hinged clamp plate 205 is fixed opposite auxiliary solenoid clamp 80. The IV tubing 18 is guided opposite solenoid 80 (the clamp plate 205 being first swung open and then closed) and then through clamping assembly 202.

The actuator 200 as shown in FIG. 7 includes a housing 210 within which is mounted a solenoid L1, and an actuator arm 212 which is mounted to pivot about point P and has fingers 214 and 216 for engaging the plunger of the clamp device (See FIG. 10). In FIG. 7 the actuator is shown in the deenergized position. When the solenoid L1 receives a high signal the actuator arm 212 rotates clockwise about point P. Opposite actuator 212 is the switch S1 with its contacts M1, K1 and K2. The clamp 80 is positioned to have a plunger 82 opposite clamp plate 205. The plunger 82 is biased to close the tubing by means of spring 84. The plunger is moved to the opposite position when coil 86 receives current. Mounted opposite plunger 82 is the switch S2.

The clamp assembly as shown in FIGS. 8 and 9 comprises a housing 220 within which is an anvil member 222 upon which rests tubing 18. Guiding means 224 in the housing guide the shaft of plunger 226. One end 228 of the shaft opposite anvil member 222 is terminated in a wedge member while the other end 230 in a collar. A leaf compression spring 232 positioned between the housing 200 and the wedge member urges the plunger 226 to the closed position. When the solenoid L1 is energized, the fingers 214 and 216 resting against the collar at end 230 urge the plunger 226 away from the anvil member 22 and the tube 18 opens. See FIG. 10. Note that stops 234 on the shaft of the plunger 226 restrict clamping motion to prevent excessive stress on tube 18.

Over a 24 hours period, the clamp 22 may be actuated more than 150,000 times. To prevent mechanical fatigue of the tube 18 and possible failure of the flow control function, it should be very lightly stressed when it is clamped closed.

As shown in FIG. 12 the conventional tube 17 when compressed has highly stressed regions 17A and 17B and even leakage channels 17C and 17D. The conventional tube is cylindrical when unstressed as shown in FIG. 11. According to a feature of the invention the tube 18 has axially fused sections 18A and 18B at diametrically opposite regions. See FIG. 13. Thus when the tube 18 is clamped shut as shown in FIG. 14 virtually no stress is required to prevent fluid flow. The fused sections move out smoothly under no restraint and there are no leakage channels.

There has thus been shown an improved method and apparatus for the delivery of IV fluids wherein the drop rate is positively controlled over a wide dynamic range by periodically opening wide a tube clamp at the desired drop rate and closing the tube clamp at the detection of each drop.

Thus the fluid is being delivered to the patient during the open periods of the clamp, and thereby is delivered at very high instantaneous flow rates. This flow rate serves to reduce the thickness of the stationary layers of the fluid at the walls of the cannula or needle and thereby reducing the probability of clotting.

While only one embodiment of the invention has been shown and described in detail there will now be obvious to those skilled in the art many modifications and variations satisfying many or all of the objects of the invention but which do not depart from the spirit thereof as defined by the appended claims. For example, instead of using analog techniques for the integrators and comparators one could use digital counting techniques.

What is claimed is:

1. In the delivery of fluids parenterally by using an intravenous device which includes a drop former and a fluid conduit connected to the drop former for delivery of fluid from the drop former to a fluid delivery means, the method of controlling the volumetric flow through the fluid conduit comprising the steps of periodically opening the fluid conduit at a frequency equal to a desired rate of drop flow, detecting each drop formed in response to the opening of the fluid conduit, closing the fluid conduit each time a drop is formed and detected, determining the size of formed drops, and varying the time of subsequent openings of the fluid conduit by times relates directly responsive to the size of the formed drops whereby a desired volumetric rate is maintained.

2. The method of claim 1 further comprising the step of giving an alarm whenever a drop is not detected within a given period of time less than the drop period after the opening of the fluid conduit.

3. The method of claim 1 further comprising the steps of monitoring the state of the conduit and giving an alarm whenever the open or closed state of the conduit is different from the desired state of the conduit.

4. In a system for delivery of fluids by means of a flow of drops, apparatus for controlling the rate of flow of the drops comprising, drop forming means for forming drops of the fluid, a fluid conduit having one end connected to said drop forming means for receiving fluid therefrom and another end for delivery of fluid, an electromechanical clamping means on said conduit, said clamping means being in a normally closed position but shifting to an open position in response to the receipt of a signal of a given level, a bistable signal generator means having input means for receiving control signals and output means connected to said electromechanical clamping means for transmitting a signal having other than the given level when in a first state and for transmitting a signal having the given level when in a second state, said input means having means for switching said bistable signal generator means to said first state upon receipt of a first control signal and for switching said bistable signal generator means to said second state upon receipt of a second control signal, source means connected to said input means for periodically generating said first control signals with a repetition rate equal to a desired drop delivery rate, drop detector means for generating one of said second control signals each time a drop is formed and delivered by said drop forming means, indicating means for giving an indication of the size of the drops detected by said drop detector means, and means for controlling the frequency of the generation of said first control signals in accordance with the indications given by said indicating means.

5. The apparatus of claim 4, wherein said source means is a signal pulse generator having a controllably variable repetition rate.

6. The apparatus of claim 4 further comprising time measuring means for measuring the time between a first control signal and the next occurring second control signal, and means response to said time measuring means for giving an alarm when said time exceeds a given duration.

7. The apparatus of claim 4 wherein said drop detecting means comprises a funnel member operatively positioned in the path of travel of drops formed by said drop forming means, said funnel member having an output end, a pair of electrodes spaced from each other at said output end by a distance which is less than the minimum drop diameter, a pair of electrical conductors respectively connected to said electrodes and disposed along the outer wall of said funnel member, and circuit means for generating one of said second control signals whenever the electrodes are electrically connected by a drop of fluid passing through the output end of said funnel means.

8. The apparatus of claim 4 wherein the portion of the fluid conduit engaged by said clamping means has a pair of diametrically opposite axially entending sections where the tubing is fused.

9. The apparatus of claim 4 further comprising means for monitoring the position of said electromechanical clamping means, and means for giving an alarm whenever said electromechanical clamping means is in a closed position whenever a second control signal is generated.

10. The apparatus of claim 4 further comprising means for monitoring the position of said electromechanical clamping means, and means for giving an alarm whenever said electromechanical clamping means is in an open position whenever a first control signal is generated.

11. The apparatus of claim 10 further comprising auxiliary clamping means for clamping said fluid conduit closed whenever an alarm is given.

12. Apparatus for detecting the passage of drops of a conductive liquid along a given path comprising a funnel means of insulative material positioned in the path for intercepting the drops, said funnel means of insulative material having an output end, first and second electrodes spaced opposite each other and only at the output end of said funnel means, first and second electrical conductors respectively connected to said first and second electrodes and fixed to the outer wall of said funnel means, and circuit means connected to said electrical conductors for generating an electrical signal whenever a drop of conductive fluid bridges said electrodes, said circuit means also including means for determining the size of said drops.

13. The apparatus of claim 12 wherein the output end of said funnel means is an opening having a circular periphery and each of said electrodes is an arcuate member disposed on said circular periphery.

14. The apparatus of claim 13 wherein each of said electrodes extends in the order of 90° around the circular periphery.

15. The apparatus of claim 12 wherein said funnel means is provided with venting openings.

* * * * *